(12) United States Patent
Inaba et al.

(10) Patent No.: US 9,085,545 B2
(45) Date of Patent: Jul. 21, 2015

(54) MACROCYCLIC TRIENE LACTONES HAVING UNCONJUGATED TRIENE STRUCTURE, ITS PRODUCTION METHOD AND ITS SYNTHETIC INTERMEDIATE

(75) Inventors: Teruhiko Inaba, Tokyo (JP); Kenya Ishida, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 13/985,071

(22) PCT Filed: Feb. 24, 2012

(86) PCT No.: PCT/JP2012/055309
§ 371 (c)(1),
(2), (4) Date: Aug. 13, 2013

(87) PCT Pub. No.: WO2012/115285
PCT Pub. Date: Aug. 30, 2012

(65) Prior Publication Data
US 2013/0324744 A1 Dec. 5, 2013

(30) Foreign Application Priority Data
Feb. 25, 2011 (JP) ................. 2011-040574

(51) Int. Cl.
| | |
|---|---|
| C07D 313/00 | (2006.01) |
| A23L 1/226 | (2006.01) |
| A23L 2/56 | (2006.01) |
| C11B 9/00 | (2006.01) |
| C11D 3/20 | (2006.01) |
| C11D 3/50 | (2006.01) |
| C11D 7/26 | (2006.01) |
| C07C 69/732 | (2006.01) |
| A61K 8/49 | (2006.01) |
| A61Q 19/00 | (2006.01) |
| A61Q 13/00 | (2006.01) |

(52) U.S. Cl.
CPC ........... *C07D 313/00* (2013.01); *A23L 1/22671* (2013.01); *A23L 2/56* (2013.01); *A61K 8/4973* (2013.01); *A61Q 19/00* (2013.01); *C07C 69/732* (2013.01); *C11B 9/0084* (2013.01); *C11D 3/2096* (2013.01); *C11D 3/50* (2013.01); *C11D 7/267* (2013.01); *A61K 2800/10* (2013.01); *A61Q 13/00* (2013.01)

(58) Field of Classification Search
CPC .................................................. C07D 313/00
USPC ........................................................ 549/266
See application file for complete search history.

(56) References Cited

U.S. PATENT DOCUMENTS

| | | | |
|---|---|---|---|
| 3,681,395 A | 8/1972 | Mookherjee et al. | |
| 2004/0122089 A1 | 6/2004 | Martin et al. | |
| 2009/0163557 A1 | 6/2009 | Makriyannis et al. | |
| 2010/0204344 A1* | 8/2010 | Kraft ............................ | 514/772 |
| 2012/0165552 A1* | 6/2012 | Ikegami et al. ............... | 549/266 |

FOREIGN PATENT DOCUMENTS

| | | |
|---|---|---|
| JP | 63-238075 A | 10/1988 |
| JP | 2008-515978 A | 5/2008 |
| WO | 2009/039675 A1 | 4/2009 |
| WO | 2011/027906 A1 | 3/2011 |

OTHER PUBLICATIONS

Office Action dated Dec. 16, 2014 issued by the Japanese Patent Office in counterpart Japanese Patent Application No. 2011-040574.
Oliver Wichmann et al.; "Probing Phospholipase A2 with Fluorescent Phospholipid Substrates"; ChemBioChem; vol. 8; No. 13; 2007; pp. 1555-1569.
Search Report, Issued by the European Patent Office; Dated Jul. 28, 2014, In counterpart European Application No. 12749923.4.
Kraft, Philip, et al., "(4E,8Z)-12-Methyloxacyclotetradeca-4,8-dien-2-one and its 7a-Homologue: Conformationally Constrained Double-Unsaturated Macrocyclic Musks by Ring Closing Alkyne Metathesis," Synthesis, Jan. 2008, pp. 543-550.
(Continued)

*Primary Examiner* — Nizal Chandrakumar
(74) *Attorney, Agent, or Firm* — Sughrue Mion, PLLC

(57) ABSTRACT

The present invention provides a novel macrocyclic compound exhibiting superior odor qualities and having a musk-like aroma, a method for producing the same, and a novel flavor or fragrance composition, and food products or beverages, fragrances or cosmetics, daily necessities or household goods and oral products using the novel macrocyclic compound. The invention relates to a compound represented by the formula (1), wherein each of wavy lines represents at least one of an E-configuration of C=C double bond and an Z-configuration of C=C double bond; m represents an integer of 0 to 10; and n represents an integer of 1 to 11, and n represents an integer of 1 to 11 when m is 0 to 4 or 6 to 10, and n is an integer of 1 or 3 to 11 when m is 5.

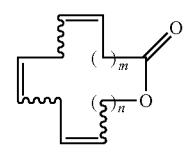

(1)

12 Claims, No Drawings

(56) References Cited

OTHER PUBLICATIONS

International Search Report (PCT/ISA/210), dated Apr. 17, 2012, issued by the International Searching Authority in counterpart International Patent Application No. PCT/JP2012/055309, Jul. 28, 2014.
Written Opinion (PCT/ISA/237), dated Apr. 17, 2012, issued by the International Searching Authority in counterpart International Patent Application No. PCT/JP2012/055309.
Bestmann, Hans Jürgen, et al., "Cumulated Ylides XX.[1] Syntheses of (E)-α,β-Unsaturated Macrocyclic Lactones by Intramolecular Wittig-Olefination via Triphenylphosphoranylideneketene[2]," Synthesis, Jun. 1989, pp. 419-423.
Villemin, Didier, "A Simple Synthesis of trans-$\Delta^9$-Isoambrettolide, Dihydroambrettolide, and Methyl 16-Acetoxy-9-hexadecenoate," Synthesis, Feb. 1987, pp. 154-155.
Ohta, Shinji, Lecture Abstract, Organizing Committee, 51st Symposium on the Chemistry of Terpenes, Essential Oils, and Aromatics, Nagahama Institute of Bio-Science and Technology, Nov. 10, 2007, pp. 199-201.
Belaidi, S., et al., "Quantitative Conformational Analysis of Dissymmetric Macrolides by Molecular Modeling," Asian Journal of Chemistry, vol. 17, No. 2, 2005, pp. 859-870.
White, James D., et al., "A Biogenetic Approach to Halicholactones. Anomalous Cyclization of an Epoxytridecadienoic Acid," Synlett, No. 1, Jan. 1996, pp. 31-33.

* cited by examiner

MACROCYCLIC TRIENE LACTONES HAVING UNCONJUGATED TRIENE STRUCTURE, ITS PRODUCTION METHOD AND ITS SYNTHETIC INTERMEDIATE

TECHNICAL FIELD

The present invention relates to a novel macrocyclic triene lactone compounds having an unconjugated triene structure commonly found in nature, a method for producing the same and the synthetic intermediate. More specifically, the present invention relates to a macrocyclic triene lactone compounds having a musk-like aroma, a method for producing the same and the synthetic intermediate. Furthermore, the present invention relates to a flavor or fragrance composition containing a macrocyclic triene lactone compound(s), and products such as food products or beverages, fragrances or cosmetics, daily necessities or household goods and oral products, which contain the compound(s) or the flavor or fragrance composition.

BACKGROUND ART

Natural musk aromas have been considered to be valued as expensive flavor or fragrances. However, animal-derived musk aromas are not easily available in terms of animal protection and plant-derived musk aromas are difficult to be stably supplied since they readily depend on weather or the like. Accordingly, synthetic compounds having a musk aroma are of a great importance. Examples of nature-derived macrocyclic lactones having a musk aroma known to date include Exaltolide found in Archangelica root oils and Ambrettolide found in Ambrette seed oils. In addition, examples of synthetic products of macrocyclic lactones include Cyclohexadecanolide and Cyclopentadecenolide (Habanolide) and the like.

Known synthesis methods of macrocyclic monoene lactones including Ambrettolide include a synthesis method using an intramolecular Wittig reaction (Non-patent Literature 1), a synthesis method starting from threo-Aleuritic acid (Non-patent Literature 2), a synthetic method using an olefin metathesis reaction (Non-patent Literature 3), and a synthetic method for 9E-isoambrettolide (Patent Literature 1) and the like. In addition, known synthetic methods of macrocyclic diene lactones include a synthetic method for 2E,8E-11-methylcycloundecadien-11-olide using an intramolecular Wittig reaction (Non-patent Literature 1), and a synthetic method using olefin metathesis reaction (Patent Literature 2). 2E,10E,12E-Cycloheptadecatrien-17-olide was reported as a macrocyclic triene lactone (Non-patent Literature 4).

In addition, Patent Literature 3 discloses 13-hydroxy-5,8,11-tridecatriynoic acid methyl ester (the formula M6 below) as ω-hydroxytriyne esters.

[Chem. 1]

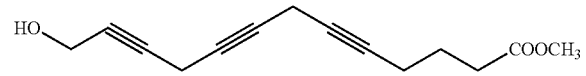

M6

Patent Literature 4 discloses 14-hydroxy-5,8,11-tetradecatriynoic acid methyl ester (the formula 5 below) as ω-hydroxytriyne esters. In addition, Patent Literature 4 discloses 14-hydroxy-5,8,11-tetradecatrienoic acid methyl ester (the formula 6 below) as ω-hydroxytriene esters.

[Chem. 2]

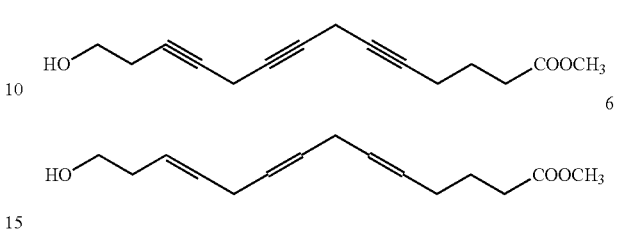

CITATION LIST

Patent Literature

[PTL 1] U.S. Pat. No. 3,681,395
[PTL 2] WO 2009/039675
[PTL 3] JP-A-2008-515978
[PTL 4] US Patent Application Publication No. 2004/122089

Non-Patent Literature

[NPL 1] Synthesis (1989), p. 419-423
[NPL 2] Synthesis (1987), p. 154-155
[NPL 3] Lecture Abstract of 51$^{th}$ Symposium on flavor or fragrance/terpenes and essential oil chemicals, p. 199-201
[NPL 4] Asian Journal of chemistry (2005), p. 859-870

SUMMARY OF INVENTION

Technical Problem

As mentioned above, various macrocyclic lactones or synthesis thereof were reported. However, macrocyclic lactones having an unconjugated triene structure and/or a synthetic method thereof are not known.

In addition, usefulness of compounds disclosed in Patent Literature 3 and Patent Literature 4 as intermediates for the preparation of flavor or fragrance compounds is not disclosed.

Accordingly, an aspect of the present invention is to provide a novel macrocyclic compound that satisfies these requirements, exhibits excellent odor quality and has a unique musk-like aroma, and a method for producing the same. Another aspect of the present invention is to provide a flavor or fragrance composition containing the macrocyclic compound having these characteristics. Yet another aspect of the present invention is to provide products such as food products or beverages, fragrances or cosmetics, daily necessities or household goods and oral products, which contain the compound or the flavor or fragrance composition.

Solution to Problem

As a result of intensive studies to solve the above-mentioned problems, the present inventors have intensive studies and found that macrocyclic triene lactones having an unconjugated triene structure commonly found in nature represented by the formula (1) has a unique musk aroma.

That is, the invention encompasses the following embodiments.

[1] A compound represented by the following formula (1):

[Chem. 3]

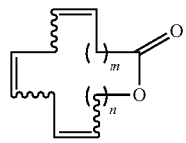

(1)

wherein each of wavy lines represents at least one of an E-configuration of C=C double bond and an Z-configuration of C=C double bond; m represents an integer of 0 to 10; and n represents an integer of 1 to 11, wherein n represents an integer of 1 to 11 when m is 0 to 4 or 6 to 10; and n is an integer of 1 or 3 to 11 when m is 5.

[2] The compound according to [1], wherein all of the wavy lines are the Z-configuration of C=C double bond.

[3] The compound according to [1] or [2], which has a musk aroma.

[4] A method for producing a compound represented by the following formula (1),

[Chem. 4]

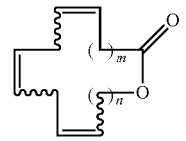

(1)

wherein each of wavy lines represents at least one of an E-configuration of C=C double bond and an Z-configuration of C=C double bond; m represents an integer of 0 to 10; and n represents an integer of 1 to 11, which comprises:

hydrogenating an ω-hydroxytriyne esters represented by the following formula (2):

[Chem. 5]

(2)

wherein m represents an integer of 0 to 10; n represents an integer of 1 to 11; and R represents a monovalent aromatic ring group having 6 to 20 carbon atoms, or a monovalent hydrocarbon group having 1 to 20 carbon atoms which may have a substituent group;

and lactonizing an ω-hydroxytriene esters represented by the following formula (3) obtained by the hydrogenation:

[Chem. 6]

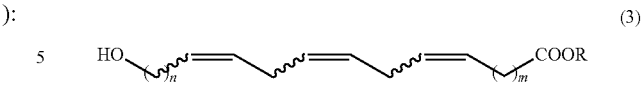

(3)

wherein m represents an integer of 0 to 10; n represents an integer of 1 to 11; and R represents a monovalent aromatic ring group having 6 to 20 carbon atoms, or a monovalent hydrocarbon group having 1 to 20 carbon atoms which may have a substituent group, and each of wavy lines represents at least one of an E-configuration of C=C double bond and an Z-configuration of C=C double bond.

[5] The method according to [4], wherein all of the wavy lines in the formula (1) are the Z-configuration of C=C double bond.

[6] The method according to [4] or [5], wherein the compound represented by the formula (1) in which all of the wavy lines are the Z-configuration of C=C double bond is produced in a ratio of 95% or more based on the whole of the produced compounds represented by the formula (1), and the rest can either be geometrical isomers.

[7] The method according to any one of [4] to [6], wherein the ω-hydroxytriene esters represented by the formula (3) is lactonized with titanate.

[8] A ω-hydroxytriyne esters represented by the following formula (2):

[Chem. 7]

(2)

wherein m represents an integer of 0 to 10; n represents an integer of 1 to 11; and R represents a monovalent aromatic ring group having 6 to 20 carbon atoms, or a monovalent hydrocarbon group having 1 to 20 carbon atoms which may have a substituent group, and a compound in which m is 3, n is 1 and R is a methyl group and a compound in which m is 3, n is 2 and R is a methyl group are excluded.

[9] A ω-hydroxytriene esters represented by the following formula (3):

[Chem. 8]

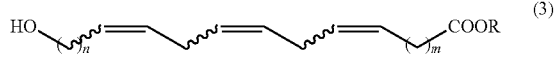

(3)

wherein m represents an integer of 0 to 10; n represents an integer of 1 to 11; and R represents a monovalent aromatic ring group having 6 to 20 carbon atoms, or a monovalent hydrocarbon group having 1 to 20 carbon atoms which may have a substituent group, and a compound in which m is 3, n is 2 and R is a methyl group is excluded, and each of wavy lines represents at least one of an E-configuration of C=C double bond and an Z-configuration of C=C double bond.

[10] The ω-hydroxytriene esters according to [9], wherein all of the wavy lines are the Z-configuration of C=C double bond.

[11] A flavor or fragrance composition comprising the compound according to any one of [1] to [3].

[12] A product comprising the compound according to any one of [1] to [3], wherein the product is selected from the group consisting of a food product or beverage, a fragrance or cosmetic, a daily necessities and household goods and an oral product.

[13] A product comprising the flavor or fragrance composition according to [11], wherein the product is selected from the group consisting of a food product or beverage, a fragrance or cosmetic, a daily necessities and household goods and an oral product.

Advantageous Effects of Invention

The compound of the present invention represented by the formula (1), that is, a macrocyclic triene lactone having an unconjugated triene structure has a musk-like aroma, in particular, unique musk-like aroma such as fruit-like, floral-like, creamy-like and animal-like. Accordingly, the compound may be effectively used directly, or in the form of a flavor or fragrance composition for a variety of products such as food products or beverages, fragrances or cosmetics, daily necessities or household goods and oral products and furthermore, can impart the desired fragrances and flavors to various products.

Also, according to the production method of the present invention, it is possible to selectively produce a compound represented by the formula (1) having a particularly excellent odor in which all C=C double bonds are in the Z-configuration among the compounds represented by the formula (1) on an industrial scale and at a high purity.

DESCRIPTION OF EMBODIMENTS

In this specification, "% by weight" and "parts by weight" have the same meanings as "% by mass" and "parts by mass", respectively.

Hereinafter, the macrocyclic triene lactone having an unconjugated triene structure according to the present invention will be described in detail.

<Compound Represented by the Formula (1)>

The macrocyclic triene lactone having an unconjugated triene structure according to the present invention is a compound represented by the formula (1) below.

[Chem. 9]

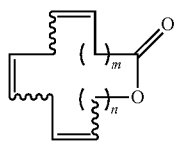

(1)

In the formula (1), each of wavy lines represents at least one of E-configuration of C=C double bond and a Z-configuration of C=C double bond. m represents an integer of 0 to 10 and n represents an integer of 1 to 11. When m represents an integer of 0 to 4 or 6 to 10, n represents an integer of 1 to 11. In addition, when m is 5, n represents an integer of 1 or 3 to 11.

The compound represented by the formula (1) is preferably a 15-membered ring compound, 16-membered ring compound or 17-membered ring compound.

As the 15-membered ring compound, in particular, compounds represented by the formula (1) satisfying (m=0, n=5), (m=1, n=4), (m=2, n=3), (m=3, n=2) and (m=4, n=1) are preferred.

As the 16-membered ring compound, in particular, compounds represented by the formula (1) satisfying (m=0, n=6), (m=1, n=5), (m=2, n=4), (m=3, n=3), (m=4, n=2) and (m=5, n=1) are preferred.

As the 17-membered ring compound, in particular, compounds represented by the formula (1) satisfying (m=0, n=7), (m=1, n=6), (m=2, n=5), (m=3, n=4), (m=4, n=3), and (m=6, n=1) are preferred.

Specifically, the compounds represented by the formula (1) include:
6,9,12-tetradecatrien-14-olide in which m is 4 and n is 1;
6,9,12-pentadecatrien-15-olide in which m is 4 and n is 2;
7,10,13-pentadecatrien-15-olide in which m is 5 and n is 1;
5,8,11-hexadecatrien-16-olide in which m is 3 and n is 4; and
6,9,12-hexadecatrien-16-olide in which m is 4 and n is 3.

Of these, the compound represented by the formula (1) is preferably a compound in which all three C=C double bonds are in the Z-configurations (hereinafter, a compound in which all C=C double bonds are in the Z-configuration will be referred to as a "Z-form") in terms of odor quality and diffusion property.

Specifically, examples of the compound include:
(6Z,9Z,12Z)-tetradecatrien-14-olide in which m is 4 and n is 1;
(6Z,9Z,12Z)-pentadecatrien-15-olide in which m is 4 and n is 2;
(7Z,10Z,13Z)-pentadecatrien-15-olide in which m is 5 and n is 1;
(5Z,8Z,11Z)-hexadecatrien-16-olide in which m is 3 and n is 4; and
(6Z,9Z,12Z)-hexadecatrien-16-olide in which m is 4 and n is 3.

The compounds represented by the formula (1) generally include, in addition to a compound (Z-form) in which three C=C double bonds are in the Z-configuration, a mixture of a compound (E-form) in which three C=C double bonds are in the E-configuration, a compound in which one C=C double bond is in the E-configuration and two C=C double bonds are in the Z-configuration, and a compound in which one C=C double bond is in the Z-configuration and two C=C double bonds are in the E-configuration. The mixture in which the ratio of the Z-form is 95% or more is preferable in terms of odor quality and diffusion property.

These compounds have each unique and attractive musk-like aroma. The term "unique and attractive musk-like aroma" refers to a musk aroma such as fruit-like, floral-like, creamy-like and animal-like aroma.

(Production Method)

Next, a production method of the macrocyclic triene lactone having an unconjugated triene structure represented by the following formula (1) according to the present invention will be described.

In the present invention, the compound represented by the formula (1) is produced by the method including hydrogenating ω-hydroxytriyne esters represented by the formula (2) and lactonizing ω-hydroxytriene esters represented by the formula (3) which is obtained by the hydrogenation.

[Chem. 10]

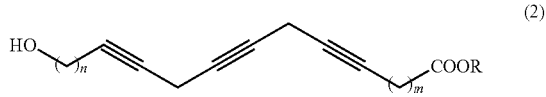

(2)

In the formula (2), m represents an integer of 0 to 10, n represents an integer of 1 to 11, and R represents a monovalent aromatic ring group having 6 to 20 carbon atoms or a monovalent hydrocarbon group having 1 to 20 carbon atoms which may have a substituent group.

[Chem. 11]

In the formula (3), m represents an integer of 0 to 10, n represents an integer of 1 to 11, and R represents a monovalent aromatic ring group having 6 to 20 carbon atoms or a monovalent hydrocarbon group having 1 to 20 carbon atoms which may have a substituent group. Each of wavy lines represents at least one of an E-configuration of C═C double bond and a Z-configuration of C═C double bond.

[Chem. 12]

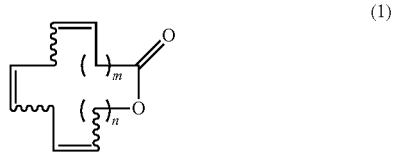

In the formula (1), each of wavy lines represents at least one of an E-configuration of C═C double bond and a Z-configuration of C═C double bond, and m represents an integer of 0 to 10, and n represents an integer of 1 to 11.

The production method of the compound represented by the formula (1) will be described in detail in accordance with the following Scheme 1.

The following description will be given under the condition that R in the formula (2) and formula (3) is a methyl group, but the present invention is not limited thereto.

<Scheme 1>

Hereinafter, Me represents a methyl group, Et represents an ethyl group and Ph represents a phenyl group, and m represents an integer of 0 to 10 and n represents an integer of 1 to 11.

[Chem. 13]

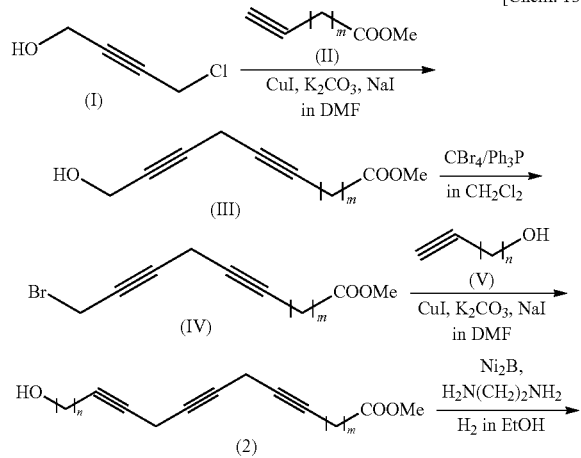

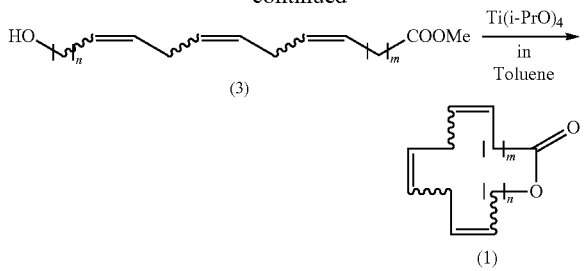

First, ω-hydroxydiyne ester (III) is obtained by coupling reaction of chlorohydrin (I) with alkyne carboxylic acid ester (II). Examples of the solvent used herein include dimethylformamide (hereinafter, also referred to "DMF"), dimethylacetamide, dimethylsulfoxide, acetonitrile and the like. The amount of the solvent used can be decided based on typical procedure in this industry. Usual choice could be of 0.1 to 100 times content (ml), more preferably 5 to 50 times content based on the weight (g) of chlorohydrin (I) as a substrate (hereafter, a unit of [solvent ml/substrate g] will be referred to as "time(s) content"). The reaction temperature is preferably 0 to 100° C., more preferably 20 to 50° C. The reaction time is 0.5 to 100 hours, preferably 3 to 60 hours.

As reaction aids, an equimolar or more amount, preferably 1 to 2 equivalent of base such as potassium carbonate, sodium carbonate, calcium carbonate and barium carbonate, and iodide such as sodium iodide, potassium iodide and lithium iodide in an amount of 0.01 to 2 equivalents, preferably 1 to 2 equivalents against chlorohydrin (I) can be used. In addition, copper iodide is used as a reaction catalyst in an amount of 0.01 to 2 equivalents, preferably 0.2 to 1 equivalents based on chlorohydrin (I).

The obtained ω-hydroxydiyne ester (III) is brominated to obtain bromodiyne ester (IV) and ω-hydroxytriyne esters (2) are obtained by coupling reaction of the bromodiyne ester with alkyne alcohol (V). The bromination of ω-hydroxydiyne ester (III) may be carried out using carbon tetrabromide and triphenyl phosphine in a dichloromethane solvent, but the present invention is not limited thereto.

The coupling reaction of the obtained bromodiyne ester (IV) with alkyne alcohol (V) may be carried out under the same conditions as coupling reaction of chlorohydrin (I) with alkyne carboxylic acid ester (II). In addition, instead of bromodiyne ester (IV), chloride, iodide, mesylate or tosylate can be used.

Next, the ω-hydroxytriyne esters represented by the formula (2) are hydrogenated to obtain ω-hydroxytriene esters represented by the formula (3).

The hydrogenation is preferably carried out in the presence of amine using nickel boride as a catalyst. As a result, a Z-form thereof can be selectively obtained. Alternatively, a Z-form thereof can be selectively obtained using a Lindlar catalyst or the like.

The amount of nickel boride used as a hydrogenation catalyst is preferably 0.1 to 5 equivalents, more preferably 0.5 to 2 equivalents based on ω-hydroxytriyne esters represented by the formula (2).

Examples of amine used for hydrogenation include quinoline, pyridine, piperidine, morpholin, triethylamine, ethylene diamine, 1,2-propylene diamine and the like. In order to improve the selectivity of the Z-form, ethylene diamine is particularly preferably used. The amount of the amine used is preferably 0.1 to 10 equivalents, more preferably 1 to 6 equivalents based on ω-hydroxytriyne esters represented by the formula (2).

Examples of the solvent used for hydrogenation include methanol, ethanol, isopropyl alcohol, ethyl acetate, butyl acetate, toluene, xylene, hexane, heptane, cyclohexane and methylcyclohexane and the like. The amount of the solvent used is preferably 3 to 100 times content (ml), more preferably 20 to 70 times content based on the weight (g) of ω-hydroxytriyne esters represented by the formula (2) as a substrate.

The hydrogenation reaction temperature is preferably 0 to 50° C., more preferably 10 to 40° C. The reaction time is preferably 0.5 to 10 hours. The reaction pressure is preferably atmospheric pressure to 10 atm, more preferably atmospheric pressure.

Next, the obtained ω-hydroxytriene esters represented by the formula (3) is lactonized to prepare a compound represented by the formula (1) as a Z-form.

For example, the lactonization may be carried out by refluxing the ω-hydroxytriene esters in a solvent using a titanate catalyst.

Examples of titanate include titanium (IV) methoxide, titanium (IV) ethoxide, titanium (IV) isopropoxide, titanium (IV) isobutoxide, titanium (IV) t-butoxide, titanium (IV) octadecyloxide and the like. The amount of titanate used is preferably 0.01 to 10 equivalents, more preferably 0.1 to 1 equivalents based on ω-hydroxytriene esters represented by the formula (3), as a substrate.

Examples of the solvent used for lactonization include benzene, toluene, xylene cyclohexane, methylcyclohexane and the like. The amount of the solvent used is preferably 1 to 2000 times content, more preferably 200 to 1000 times content, based on ω-hydroxytriene esters represented by the formula (3), as a substrate.

The reaction temperature of the lactonization is preferably 50 to 200° C., more preferably 80 to 150° C. The reaction time is preferably 0.5 to 20 hours, more preferably 3 to 10 hours.

In addition, the Z-form compound represented by the formula (1) can be obtained, instead of the lactonization, by polymerization and depolymerization in which the ω-hydroxytriene esters represented by the formula (3) is heated to prepare an oligomer thereof and the oligomer is heated under reduced pressure to perform depolymerization.

According to the production method, a Z-form compound is selectively obtained at a high purity among the compounds represented by the formula (1). In particular, the Z-form can be obtained with the purity of 95% or more.

Specifically, examples of the compound represented by the formula (1) obtained by the production method include:
(7Z,10Z,13Z)-hexadecatrien-16-olide in which m is 5 and n is 2;
(6Z,9Z,12Z)-tetradecatrien-14-olide in which m is 4 and n is 1;
(6Z,9Z,12Z)-pentadecatrien-15-olide in which m is 4 and n is 2;
(7Z,10Z,13Z)-pentadecatrien-15-olide in which m is 5 and n is 1;
(5Z,8Z,11Z)-hexadecatrien-16-olide in which m is 3 and n is 4; and
(6Z,9Z,12Z)-hexadecatrien-16-olide in which m is 4 and n is 3.

The Z-form compound represented by the formula (1) obtained by the production method has a musk aroma, in particular, unique musk aroma such as fruit-like, floral-like, creamy-like, animal-like.

<Compounds Represented by the Formula (2) and Formula (3)>

Next, the compounds represented by the formula (2) and formula (3) according to the present invention, as intermediates of the production method of the compound represented by the formula (1), will be described.

The ω-hydroxytriyne esters represented by the formula (2) will be given as follows.

[Chem. 14]

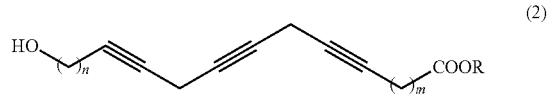

In the formula (2), m represents an integer of 0 to 10, and n represents an integer of 1 to 11. R represents a monovalent aromatic ring group having 6 to 20 carbon atoms, or a monovalent hydrocarbon group having 1 to 20 carbon atoms which may have a substituent group.

The ω-hydroxytriene esters represented by the formula (3) will be given as follows.

[Chem. 15]

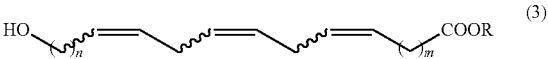

In the formula (3), m represents an integer of 0 to 10 and n represents an integer of 1 to 11. R represents a monovalent aromatic ring group having 6 to 20 carbon atoms, or a monovalent hydrocarbon group having 1 to 20 carbon atoms which may have a substituent group. Each of wavy lines represents at least one of an E-configuration of C=C double bond and a Z-configuration of C=C double bond.

The compound represented by the formula (3) is preferably a compound in which all three C=C double bonds are in the Z-configuration, and particularly preferably, the compound in which three C=C double bonds are Z-configuration is present at 95% or more.

The R in the formulae (2) and (3), which is a monovalent aromatic ring group having 6 to 20 carbon atoms or a monovalent hydrocarbon group having 1 to 20 carbon atoms which may have a substituent group, will be described.

Examples of the monovalent aromatic ring group having 6 to 20 carbon atoms include a phenyl group, a tolyl group, a benzyl group, a naphthyl group and the like. In addition, the number of carbon atoms is preferably 6 to 10.

Examples of the monovalent hydrocarbon group having 1 to 20 carbon atoms which may have a substituent group, include a linear or branched hydrocarbon group and a cyclic hydrocarbon group, and the monovalent hydrocarbon group may contain a carbon-carbon unsaturated bond. In addition, the number of carbon atoms is preferably 1 to 12. Examples of the monovalent hydrocarbon group include an alkyl group, an alkenyl group, an alkynyl group, a cycloalkyl group, a cycloalkenyl group and the like.

Examples of the alkyl group include a methyl group, an ethyl group, an n-propyl group, an isopropyl group, an n-butyl group, a sec-butyl group, a tert-butyl group, an n-pentyl group, an n-hexyl group, an n-heptyl group, an octyl group, a nonyl group and the like.

Examples of the alkenyl group include a vinyl group, an allyl group, a propenyl group, an isopropenyl group, a 2-methyl-1-propenyl group, a methallyl group, a 2-butenyl group and the like.

Examples of the alkynyl group include an ethynyl group, a propynyl group, a butynyl group and the like.

Examples of the cycloalkyl group include a cyclobutyl group, a cyclopentyl group, a cyclohexyl group, a cycloheptyl group, a cyclooctyl group and the like.

Examples of the cycloalkenyl group include a cyclobutenyl group, a cyclopentenyl group, a cyclohexenyl group and the like.

Examples of the substituent that the monovalent hydrocarbon group having 1 to 20 carbon atoms may have include a phenyl group, a tolyl group, a benzyl group, a naphthyl group and the like.

In the formula (2) and formula (3), R is preferably a methyl group, an ethyl group or the like, but is not limited thereto.

In the formula (2) and formula (3), m is 0 to 10 and n is 1 to 11.

Compounds that satisfying (m=0, n=5), (m=1, n=4), (m=2, n=3), (m=3, n=2), or (m=4, n=1) in the formula (2) and formula (3) are preferred as intermediates of 15-membered ring compounds represented by the formula (1).

Compounds that satisfying (m=0, n=6), (m=1, n=5), (m=2, n=4), (m=3, n=3), (m=4, n=2), or (m=5, n=1) in the formula (2) and formula (3) are preferred as intermediates of 16-membered ring compounds represented by the formula (1).

Compounds that satisfying (m=0, n=7), (m=1, n=6), (m=2, n=5), (m=3, n=4), (m=4, n=3), (m=5, n=2), or (m=6, n=1) in the formula (2) and formula (3) are preferred as intermediates of 17-membered ring compounds represented by the formula (1).

Specifically, the compounds represented by the formula (2) include:

methyl 16-hydroxyhexadeca-7,10,13-triynoate in which m is 5, n is 2 and R is methyl;

methyl 14-hydroxytetradeca-6,9,12-triynoate in which m is 4, n is 1 and R is methyl;

methyl 15-hydroxypentadeca-6,9,12-triynoate in which m is 4, n is 2 and R is methyl;

methyl 15-hydroxypentadeca-7,10,13-triynoate in which m is 5, n is 1 and R is methyl;

methyl 16-hydroxyhexadeca-5,8,11-triynoate in which m is 3, n is 4 and R is methyl; and methyl 16-hydroxyhexadeca-6,9,12-triynoate in which m is 4, n is 3 and R is methyl.

Specifically, the compounds represented by the formula (3) include:

methyl 16-hydroxyhexadeca-(7Z,10Z,13Z)-trienoate in which m is 5, n is 2 and R is methyl;

methyl 14-hydroxytetradeca-(6Z,9Z,12Z)-trienoate in which m is 4, n is 1 and R is methyl;

methyl 15-hydroxypentadeca-(6Z,9Z,12Z)-trienoate in which m is 4, n is 2 and R is methyl;

methyl 15-hydroxypentadeca-(7Z,10Z,13Z)-trienoate in which m is 5, n is 1 and R is methyl;

methyl 16-hydroxyhexadeca-(5Z,8Z,11Z)-trienoate in which m is 3, n is 4 and R is methyl; and methyl 16-hydroxyhexadeca-(6Z,9Z,12Z)-trienoate, in which m is 4, n is 3 and R is methyl.

The compounds represented by the formula (2) and formula (3) are useful as intermediates for producing the compound represented by the formula (1).

In addition, all compounds excluding the compound represented by the formula (2) in which m is 3, n is 1 and R is a methyl group and compounds represented by the formulae (2) and (3) in which m is 3, n is 2 and R is a methyl group are novel compounds.

(Food Products or Beverages, Fragrances or Cosmetics, Daily Necessities and Household Goods, and Oral Products)

The compound of the present invention represented by the formula (1) can be used as a flavor or fragrance compound for imparting fragrance or flavor to various products such as food products or beverages, fragrances or cosmetics, daily necessities and household goods, and oral products.

As the food products or beverages to which the flavor is imparted by the compound of the present invention represented by the formula (1), examples thereof include drinks such as fruit juice drinks, fruit wines, milk drinks, carbonated drink, soft drink and drink preparations; frozen sweets such as ice creams, sherbets and ice candies; desserts such as jelly and pudding; Western style confections such as cake, cookie, chocolate and chewing gum; Japanese style confections such as bean-jam bun, sweet beans jelly and Uiro; jams; candies; breads; tea drinks or luxury drinks such as green tea, Oolong tea, black tea, persimmon leaf tea, chamomile tea, low striped bamboo tea, mulberry tea, Dokudami tea, Pu-erh tea, Mate tea, Rooibos tea, Gymnema tea, Guava tea, coffee and cocoa; soups such as Japanese style soup, Western style soup and Chinese soup; flavoring and seasoning; various instant drinks or convenience foods; various snack foods and the like.

As the fragrances or cosmetics to which the fragrance is imparted by the compound of the present invention represented by the formula (1), examples thereof include fragrance products, foundation cosmetics, finishing cosmetics, hair cosmetics, sun care cosmetics, medicated cosmetics and the like.

More illustratively, examples thereof include, as the fragrance products, perfume, eau de perfume, eau de toilette, eau de cologne and the like;

as the foundation cosmetics, facial cleansing cream, banishing cream, cleansing cream, cold cream, massage cream, milky lotion, skin lotion, beauty lotion, pack, makeup remover and the like;

as the finishing cosmetics, foundation, face powder, solid face powder, talcum powder, rouge, lip barm, lip cream, cheek rouge, eye liner, mascara, eye shadow, eyebrow pencil, eye pack, nail enamel, enamel remover and the like;

as the hair cosmetics, pomade, brilliantine, set lotion, hair stick, hair solid, hair oil, hair treatment, hair cream, hair tonic, hair liquid, hair spray, bandrine, revitalizing hair tonic, hair dye and the like;

as the sun care cosmetics, suntan products, sunscreen product and the like; and as the medicated cosmetics, antiperspirant, after shaving lotion, gel, permanent wave agent, medicated soap, medicated shampoo, medicated skin cosmetics and the like.

As the dialy necessities and household goods to which the fragrance or flavor is imparted by the compound of the present invention represented by the formula (1), examples thereof include hair care products, soap, body washers, bath agents, cleansers, soft finishing agents, detergents, kitchen cleaners, bleachers, aerosols, deodorants or aromatics, household goods, shaving products, skin care products, repellents, cigarette products, and the like.

More illustratively, examples thereof include, as the hair care products, shampoo, rinse, rinse-in-shampoo, conditioner, treatment, hair pack and the like;

as the soap, toilet soap, bath soap, perfume soap, transparent soap, synthetic soap and the like;

as the body washers, body soap, body shampoo, hand soap and the like;

as the bath agents, bathing agents (bath salt, bath tablet, bath liquid and the like), foam bath (bubble bath and the like), bath oil (bath perfume, bath capsule and the like), milk bath, bath jelly, bath cube and the like;

as the detergents, heavy detergent for clothing use, light detergent for clothing use, liquid detergent, washing soap, compact detergent, powder soap and the like;

as the soft finishing agents, softener, furniture care and the like;

as the cleaners, cleanser, house cleaner, toilet cleaner, bath cleaner, glass cleaner, mildew remover, cleaner for drainpipe use and the like;

as the kitchen cleaners, kitchen soap, kitchen synthetic soap, tableware cleaner and the like;

as the bleachers, oxidation type bleacher (chlorine type bleacher, oxygen type bleacher and the like), reduction type bleacher (sulfur type bleacher and the like), optical bleacher and the like;

as the aerosols, spray type, powder spray and the like;

as the deodorants or aromatics, solid type, gel type, liquid type and the like;

as the household goods, tissue paper, toilet paper and the like;

as the shaving products, shaving foams and the like; and as the skin care products, hand cream, body cream, body lotion and the like.

Examples of the oral products to which the fragrance or flavor is imparted by the compound of the present invention represented by the formula (1) include toothpaste, mouth cleansing agents, mouthwashes, troche, chewing gums and the like.

The content of the compound of the present invention represented by the formula (1) in the food products or beverages is preferably $1\times10^{-10}$ to 0.01% by weight, more preferably $1\times10^{-7}$ to 0.001% by weight based on the total weight of the food products or beverages.

The content of the compound of the present invention represented by the formula (1) in the fragrances or cosmetics is preferably 0.00001 to 0.3% by weight, more preferably 0.001 to 0.05% by weight by weight based on the total weight of the fragrances or cosmetics.

The content of the compound of the present invention represented by the formula (1) in the daily necessities and household goods is preferably 0.00001 to 0.3% by weight, more preferably 0.001 to 0.05% by weight based on the total weight of the daily necessities and household goods.

The content of the compound of the present invention represented by the formula (1) in the oral product is preferably $1\times10^{-7}$ to 0.001% by weight, more preferably $1\times10^{-5}$ to 0.0001% by weight based on the total weight of the oral product.

<Flavor or Fragrance Composition>

The compound of the present invention represented by the formula (1) may constitute a flavor or fragrance composition together with other flavor or fragrance components.

Examples of other flavor or fragrance component that can be contained in the flavor or fragrance composition in conjunction with the compound of the present invention represented by the formula (1) include synthetic aromachemicals; materials of natural origine such as essential oils, oleoresin, extracts, animal aromachemicals, and the like.

Any synthetic aromachemicals may be used for the flavor or fragrance composition of the present invention without particular limitation so long as it has been used in the related art to impart fragrances and flavors. Examples of synthetic aromachemicals include flavor or fragrance components disclosed in "Synthetic aromachemical: Chemistry and Product Knowledge" (published on Mar. 6, 1996, written by Motoichi Indo, The Chemical Daily Co., Ltd.), and "Perfume and Flavor Chemicals (Aroma Chemicals) 1, 2" (Steffen Arctender (1969)).

As the synthetic aromachemical, examples thereof include at least one selected from the group consisting of esters, alcohols, aldehydes, ketones, phenols, ethers, lactones, hydrocarbons, nitrogen-containing compounds, sulfur-containing compounds and acids.

Examples of the esters include propyl formate, butyl formate, amyl formate, octyl formate, linalyl formate, citronellyl formate, geranyl formate, neryl formate, terpinyl formate, ethyl acetate, isopropyl acetate, isoamyl acetate, hexyl acetate, cis-3-hexenyl acetate, trans-2-hexenyl acetate, octyl acetate, nonyl acetate, decyl acetate, dodecyl acetate, dimethylundecadienyl acetate, styrallyl acetate, ocimenyl acetate, myrcenyl acetate, dihydromyrcenyl acetate, linalyl acetate, citronellyl acetate, geranyl acetate, neryl acetate, acetate of tetrahydromugol, lavandulyl acetate, nerolidyl acetate, dihydrocuminyl acetate, terpinyl acetate, citryl acetate, nopyl acetate, dihydroterpinyl acetate, 2,4-dimethyl-3-cyclohexenylmethyl acetate, miraldyl acetate, veticol acetate, decenyl propionate, linalyl propionate, geranyl propionate, neryl propionate, terpinyl propionate, tricyclodecenyl propionate, styrallyl propionate, anisyl propionate, octyl butyrate, neryl butyrate, cinnamyl butyrate, isopropyl isobutyrate, octyl isobutyrate, linalyl isobutyrate, neryl isobutyrate, linalyl isovalerate, terpinyl isovalerate, phenylethyl isovalerate, 2-methyl-2-methylpentyl valerate, methyl 3-hydroxyhexanoate, ethyl 3-hydroxyhexanoate, methyl octanoate, octyl octanoate, linalyl octanoate, methyl nonanoate, methyl undecylenate, linalyl benzoate, methyl cinnamate, isoprenyl angelicate, methyl gallate, triethyl citrate, ethyl acetoacetate, ethyl 2-hexylacetoacetate, ethyl benzyl acetoacetate, allyl 2-ethylbutyrate, ethyl 3-hydroxybutyrate, ethyl nonanoate, ethyl decanoate, ethyl 2,4-decadienoate, propyl 2,4-decadienoate, methyl anthranilate and linalyl anthranilate, ethyl N-methylanthranilate and the like.

Examples of the alcohols include 3-heptanol, 1-nonanol, 1-undecanol, 2-undecanol, 1-dodecanol, prenol, 10-undecen-1-ol, dihydrolinalool, tetrahydromugol, myrcenol, dihydromyrcenol, tetrahydromyrcenol, ocimenol, terpineol, hotrienol, 3-thujanol, benzyl alcohol, β-phenylethylalcohol, α-phenylethylalcohol, 3-methyl-1-pentanol, 1-heptanol, 2-heptanol, 3-octanol, 1-nonanol, 2-nonanol, 2,6-dimethylheptanol, 1-decanol, trans-2-hexenol, cis-4-hexenol, methyltrimethylcyclopentenylbutenol, citronellol, dihydromyrcenol, rhodinol, geraniol, nerol, linalool, tetrahydrolinalool, dimethyloctanol, hydroxycitronellol, isopulegol, menthol, terpineol, dihydroterpineol, carveol, dihydrocarveol, perilla alcohol, 4-thujanol, myrtenol, α-fenchyl alcohol, farnesol, nerolidol, cedrenol, Anise alcohol, hydratropic alcohol, 3-phenylpropyl alcohol, cinnamic alcohol, amylcinnamic alcohol and the like.

Examples of the aldehydes include acetaldehyde, n-hexanal, n-heptanal, n-octanal, n-nonanal, 2-methyloctanal, 3,5,5-trimethylhexanal, decanal, undecanal, 2-methyldecanal, dodecanal, tridecanal, tetradecanal, trans-2-hexenal, trans-4-decenal, cis-4-decenal, trans-2-decenal, 10-undecenal, trans-2-undecenal, trans-2-dodecenal, 3-dodecenal, trans-2-tridecenal, 2,4-hexadienal, 2,4-decadienal, 2,4-dodecadienal, 5,9-dimethyl-4,8-decadienal, citral, dimethyloctanal, α-methylene citronellal, citronellyloxyacetaldehyde, myrtenal, neral, α- or β-cinensal, myrac aldehyde, phenylacetaldehyde, octanal dimethyl acetal, nonanal dimethyl acetal, decanal dimethyl acetal, decanal diethyl acetal, 2-methylundecanal dimethyl acetal, citral dimethyl acetal, citral diethyl acetal, citral propylene glycol acetal, n-valeraldehyde, isovaleraldehyde, 2-methylbutanal, 2-pentenal, trans-2-heptenal, trans-2-nonenal, 2,6-dimethyl-5-heptenal, 2,4-undedienal, trimethyldecadienal, citronellal, hydroxycitronellal, safranal, Vernaldehyde, benzaldehyde, p-isopropylphenylacetaldehyde, p-methylhydrotropaldehyde, phenylpropionaldehyde, 2-methyl-3-(4-methylphenyl)propanal, cyclamen aldehyde, cinnamic aldehyde, salicylic aldehyde, anisaldehyde, p-methylphenoxyacetaldehyde, acetaldehydediethylacetal, citronellylmethylacetal, acetaldehyde-2-phenyl-2,4-pentanediol acetal, 2-hexenaldiethylacetal, cis-3-hexenal diethyl acetal, heptanal diethyl acetal, 2-hexyl-5-methyl-1,3-dioxolane, citronellal cyclomonoglycol acetal, hydroxyl citronellal dimethyl acetal, phenylacetaldehyde dimethyl acetal and the like.

Examples of the ketones include 2-pentanone, 3-hexanone, 2-heptanone, 3-heptanone, 4-heptanone, 2-octanone, 3-octanone, 2-nonanone, 2-undecanone, methylheptenone, dimethyl octenone, geranyl acetone, farnesyl acetone, 2,3,5-trimethyl-4-cyclohexenyl-1-methylketone, nerone, nootkatone, dihydronootkatone, acetophenone, 4,7-dihydro-2-isopentyl-2-methyl-1,3-dioxepine, 2,3-hexadione, 3-nonanone, ethylisoamylketone, diacetyl, amylcyclopentenone, 2-cyclopentylcyclopentanone, hexylcyclopentanone, heptylcyclopentanone, cis-jasmone, dihydrojasmone, trimethylpentylcyclopentanone, 2-(2-(4-methyl)-3-cyclohexen-1-yl)propyl cyclopentanone, damascone, α-dynascone, trimethylcyclohexenylbutenone, ionone, methylionone, allylionone, plicatone, cashmeran, l-carvone, menthone, camphor, p-methylacetophenone, p-methoxyacetophenone, benzylidene acetone, raspberry ketone, methylnaphthyl ketone, benzophenone, furfural acetone, homofuronol, maltol, ethyl maltol, ethylacetoacetate ethyleneglycol ketal and the like.

Examples of the phenols include thymol, carvacrol, β-naphtholisobutylether, anethole, β-naphtholmethylether, β-naphtholethylether, creosol, veratrole, hydroquinonedimethylether, 2,6-dimethoxyphenol, 4-ethylguaiacol, eugenol, isoeugenol, ethylisoeugenol, tert-butylhydroquinonedimethylether and the like.

Examples of the ethers include decylvinylether, α-terpenylmethylether, isoproxen, 2,2-dimethyl-5-(1-methyl-1-propenyl)-tetrahydrofuran, rosefuran, 1,4-cineol, nerol oxide, 2,2,6-trimethyl-6-vinyltetrahydropyran, methylhexylether, ocimene epoxide, limonene oxide, rhubofix, caryophyllene oxide, linalool oxide, 5-isoprophenyl-2-methyl-2-vinyltetrahydrofuran, nerol oxide, rose oxide and the like.

Examples of lactones include γ-undecalactone, δ-dodecalactone, γ-hexylactone, γ-nonalactone, γ-decalactone, γ-dodecalactone, jasmine lactone, methyl γ-decalactone, 7-decenolactone, jasmolactone, propylidene phthalide, δ-hexylactone, δ-2-decenolactone, ε-dodecalactone, dihydrocoumarin, coumarin and the like.

Examples of the hydrocarbons include ocimene, limonene, α-phellandrene, terpinene, 3-carene, bisabolene, valencene, alloocimene, myrcene, farnesene, α-pinene, β-pinene, camphene, terpinolene, p-cymene, cedrene, β-caryophyllene, cadinene and the like.

Examples of the nitrogen-containing compounds or sulfur-containing compounds include methyl anthranilate, ethyl anthranilate, methyl N-methyl anthranilate, methyl N-2'-methylpentylidene anthranilate, ligantral, dodecanenitrile, 2-tridecenenitrile, geranylnitrile, citronellylnitrile, 3,7-dimethyl-2,6-nonadienenitrile, indole, 5-methyl-3-heptanone oxime, limonene thiol, 1-p-menthene-8-thiol, butyl anthranilate, cis-3-hexenyl anthranilate, phenylethyl anthranilate, cinnamyl anthranilate, dimethyl sulfide, 8-mercapto menthone and the like.

Examples of the acids include acetic acid, propionic acid, butyric acid, valeric acid, hexanoic acid, octanoic acid, decanoic acid, dodecanoic acid, 2-decenoic acid, geranic acid, 2-methylbutyric acid, 2-ethylbutyric acid, phenylacetic acid, cinnamic acid, isobutyric acid, isovaleric acid, 3-methylvaleric acid, 2-hexenoic acid, 2-methyl-2-pentenoic acid, 2-methylheptanoic acid, myristic acid, stearic acid, lactic acid, pyruvic acid, cyclohexane carboxylic acid and the like.

The synthetic aromachemical is commercially available or easily synthesized as necessary. The material of natural origins is also commercially available or easily extracted and purified by a commonly used method.

The content of the compound of the present invention represented by the formula (1) in the flavor or fragrance composition is suitably determined depending on the type or the application of flavor or fragrance composition and is generally preferably $1 \times 10^{-8}$ to 50% by weight, more preferably $5 \times 10^{-6}$ to 5% by weight, based on the total weight of the flavor or fragrance composition, but is not particularly limited thereto.

The flavor or fragrance composition of the present invention may further contain a carrier for flavor or fragrance. The carrier for flavor or fragrance which is used in the present invention may be a liquid carrier or a solid carrier.

Examples of the liquid carrier include water; lower alcohols such as ethanol, propanol, isopropanol and butanol; glycerin; propylene glycol; triacetin and the like.

Examples of the solid carrier include natural gum substances such as Arabic gum and Tragacanth gum, surfactants (for example, non-ionic surfactants such as glycerin fatty acid ester and sucrose fatty acid ester, anionic surfactants, cationic surfactant and amphiprotic surfactants), excipients (such as gelatin, dextrin), and an encapsulating agent (such as cyclodextrin).

The flavor or fragrance composition of the present invention may be prepared in the form of a stabilization or dispersion by solubilizing or emulsion-dispersing components in a solid carrier such as a natural gum and a surfactant. Alternatively, the flavor or fragrance composition of the present invention may be provided in the form of a powder coated with natural gums such as Arabic gum or excipients such as gelatin and dextrin, or may be microcapsulated by treating with a capsulating agent. Furthermore, the flavor or fragrance composition of the present invention can be stabilized and sustained-released by encapsulating with an encapsulating agent such as cyclodextrin.

In addition, the carrier for flavor or fragrance may be used alone or in combination thereof.

The flavor or fragrance composition of the present invention may further contain a flavor or fragrance retaining agent. Examples of the flavor or fragrance retaining agent used in the present invention include known flavor or fragrance retaining agent materials used for the flavor or fragrance composition, such as glycerin, glyceride, dipropylene glycol, triethylcitrate, benzyl benzoate, benzyl salicylate and diethylphthalate.

These flavor or fragrance retaining agents may be used alone or in combination thereof.

The flavor or fragrance composition of the present invention may further contain an antioxidant such as α-Tocopherol and BHT.

When fragrances and flavors are imparted to the various products using the flavor or fragrance composition of the present invention, the flavor or fragrance composition of the present invention used may be suitable determined depending on the type or final forms of products to which fragrances and flavors are imparted (for example, product forms such as liquid, solid, powder, gel, mist and aerosol).

When fragrances and flavors are imparted to the various products using the flavor or fragrance composition of the present invention, the amount of the flavor or fragrance composition of the present invention used can be adjusted depending on the type and form of various products and effects or action required for products.

When the flavor composition is used for food products or beverages, the content of the compound represented by the formula (1) in the flavor or fragrance composition of the present invention is preferably adjusted to $1\times10^{-10}$ to 0.01% by weight, more preferably $1\times10^{-7}$ to 0.001% by weight based on the total weight of the food products or beverages.

When the flavor or fragrance composition is used for fragrances or cosmetics, the content of the compound represented by the formula (1) in the flavor or fragrance composition of the present invention is preferably adjusted to 0.00001 to 0.3% by weight, more preferably 0.001 to 0.05% by weight based on the total weight of the fragrances or cosmetics.

When the flavor or fragrance composition is used for daily necessities and household goods, the content of the compound represented by the formula (1) in the flavor or fragrance composition of the present invention is preferably adjusted to 0.00001 to 0.3% by weight, more preferably 0.001 to 0.05% by weight based on the total weight of the daily necessities and household goods.

When the flavor or fragrance composition is used for oral products, the content of the compound represented by the formula (1) in the flavor or fragrance composition of the present invention is preferably adjusted to $1\times10^{-7}$ to 0.001% by weight, more preferably $1\times10^{-5}$ to 0.0001% by weight based on the total weight of the oral products.

EXAMPLES

Hereinafter, the present invention will be described in detail with reference to the following examples, but the present invention is not limited to these examples. In addition, apparatuses used for measurement of physical properties and the like in the following examples are as follows.

NMR measurement apparatus: DRX 500 (Bruker Co., Ltd.)
Gas chromatograph: GC 353B (GL Science)
  Capillary column: TC-1 (15 m×0.53 mm)
  Column temperature: 100→250° C. (elevation of temperature at 10° C./min)
  Injection temperature: 250° C.
  Detector temperature: 250° C.

Synthesis Flow of Example 1 to 6

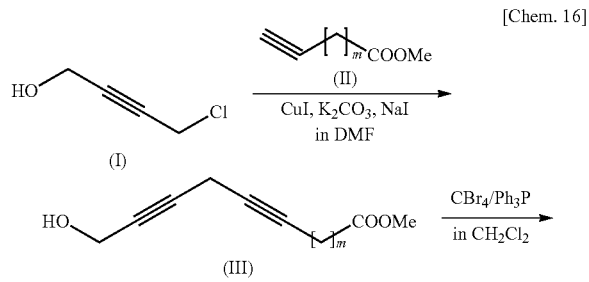

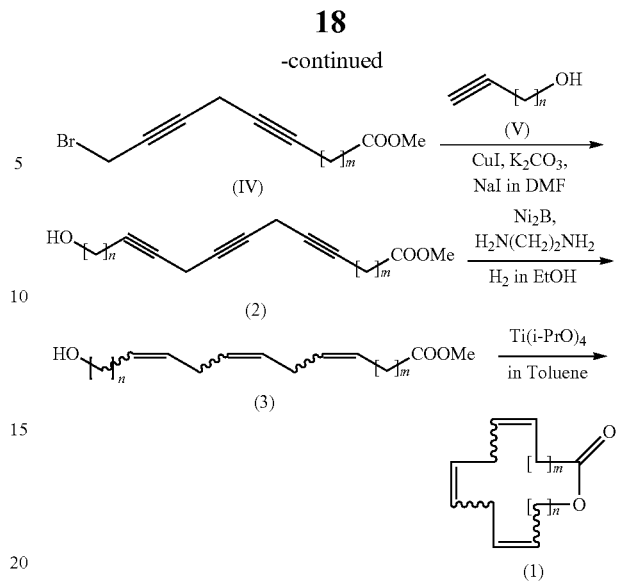

Example 1

Synthesis of (7Z,10Z,13Z)-hexadecatrien-16-olide [Formula (1); m=5, n=2]

(A) Synthesis of Methyl 12-Hydroxydodeca-7,10-diynoate [(III); m=5]

23.00 g (0.22 mol) of 4-chloro-2-butyn-1-ol (I), 33.93 g (0.22 mol) of methyl 7-octynoate (II), 30.41 g (0.22 mol) of $K_2CO_3$, 32.98 g (0.22 mol) of NaI, and 20.95 g (0.11 mol) of CuI were added to 440 ml of DMF, followed by stirring at 30° C. for 48 hours. The reaction mixture was quenched by adding to a saturated aqueous $NH_4Cl$ solution (200 ml) (hereinafter, referred to as "sat. $NH_4Cl$ aq."), then the resulting mixture was extracted with ethyl acetate. The extract was washed with water, concentrated, and the concentrate was purified over a silica gel column (hexane/ethyl acetate=8/2 to 4/6 (volume ratio)) to obtain 30.97 g of methyl 12-hydroxydodeca-7,10-diynoate having a GC purity of 93.3% (yield: 59.1% th). The structure thereof was confirmed by NMR.

$^1$H NMR (500 MHz, $CDCl_3$) δppm:
4.26 (2H, s), 3.68 (3H, s), 3.18 (2H, t, J=2.3 Hz), 2.33 (2H, t, J=7.5 Hz), 2.15-2.19 (2H, m), 1.80 (1H, bs), 1.40-1.67 (6H, m).

(B) Synthesis of methyl 12-Bromododeca-7,10-diynoate [(IV); m=5]

30.97 g (0.139 mol) of methyl 12-hydroxydodeca-7,10-diynoate obtained in (A) and 69.31 g (0.209 mol) of carbon tetrabromide were added to 500 ml of dichloromethane. The solution was stirred under ice cooling and 54.82 g (0.209 mol) of triphenyl phosphine was added thereto over one hour. After addition, the solution was stirred at room temperature for one hour to complete the reaction. The reaction mixture was concentrated under reduce pressure, followed by filtering on a celite, and a cake was washed with ether. The ether solution was concentrated, followed by purifying on a silica gel column (hexane/ethyl acetate=9/1 to 6/4 (volume ratio)) to obtain 30.08 g of methyl 12-bromododeca-7,10-diynoate having a GC purity of 94.2% (yield: 76.5% th). The structure thereof was confirmed by NMR.

¹H NMR (500 MHz, CDCl₃) δppm:
3.92 (2H, s), 3.67 (3H, s), 3.20-3.23 (2H, m), 2.32 (2H, t, J=7.5 Hz), 2.15-2.19 (2H, m), 1.36-1.67 (6H, m).

(C) Synthesis of methyl 16-hydroxyhexadeca-7,10,13-triynoate [Formula (2); m=5, n=2, R=methyl]

30.08 g (purity of 94.2%, 0.105 mol) of methyl 12-bromododeca-7,10-diynoate obtained in (B) above, 8.83 g (0.126 mol) of 3-butyn-1-ol (V), 14.51 g (0.105 mol) of K₂CO₃, 15.74 g (0.105 mol) of NaI, and 10.00 g (0.0525 mol) of CuI were added to DMF (200 ml), followed by stirring at 30° C. for 28 hours. The reaction mixture was quenched by adding to sat. NH₄Cl aq. (80 ml), then the resulting mixture was extracted with ethyl acetate, and the extract was washed with water. The organic layer was concentrated, followed by purifying on a silica gel column (hexane/ethyl acetate=7/3 to 4/6 (volume ratio)) to obtain 21.70 g of methyl 16-hydroxyhexadeca-7,10,13-triynoate having a GC purity of 95.3% (yield: 75.9% th). The structure thereof was confirmed by NMR.
¹H NMR (500 MHz, CDCl₃) δppm:
3.71 (2H, t, J=6.3 Hz), 3.67 (3H, s), 3.15-3.17 (2H, m), 3.12-3.14 (2H, m), 2.43-2.46 (2H, m), 2.32 (2H, t, J=7.6 Hz), 2.14-2.18 (2H, m), 1.85 (1H, bs), 1.38-1.67 (6H, m).

(D) Synthesis of methyl 16-hydroxyhexadeca-(7Z,10Z,13Z)-trienoate [Formula (3); m=5, n=2, R=methyl]

19.66 g (0.079 mol) of (CH₃COO)₂Ni·4H₂O was added to 1000 ml of 95% ethanol, 79 ml of a 1M NaBH₄ ethanol solution was further added thereto to prepare a Ni₂B ethanol suspension. 21.70 g (0.079 mol) of the methyl 16-hydroxyhexadeca-7,10,13-triynoate obtained in (C) and 19.00 g (0.316 mol) of ethylene diamine were added to 50 ml of ethanol, and the resulting solution was added to the above prepared Ni₂B ethanol suspension, and hydrogenation was performed for one hour.
The catalyst was separated by filtration and the filtrate was diluted with isopropyl ether and washed with saturated brine. The residue was concentrated, followed by purifying on a column (hexane/ethyl acetate=7/3 to 4/6 (volume ratio)) to obtain 14.73 g of methyl 16-hydroxyhexadeca-(7Z,10Z,13Z)-trienoate having a GC purity of 96.1% (yield 67.0% th). The structure thereof was confirmed by NMR.
¹H NMR (500 MHz, CDCl₃) δppm
5.33-5.44 (6H, m), 3.67 (3H, s), 3.63-3.65 (2H, m), 2.79-2.86 (2H, m), 2.29-2.39 (4H, m), 2.02-2.09 (2H, m), 1.66 (1H, bs), 1.58-1.65 (2H, m), 1.29-1.40 (6H, m).

(E) Synthesis of (7Z,10Z,13Z)-Hexadecatrien-16-olide [Formula (1); m=5, n=2]

14.72 g (52.5 mmol) of methyl 16-hydroxyhexadeca-(7Z,10Z,13Z)-trienoate obtained in (D) and 7.44 g (26.2 mmol) of titanium (IV) isopropoxide (Ti(i-PrO)₄) were added to 9000 ml of toluene, then the resulting mixture was refluxed for 8 hours. After cooling, the reaction mixture was quenched by addition of water, organic layer was separated, and washed with saturated brine. The resulting solution was concentrated, followed by purifying on a column (hexane/ethyl acetate=95/5 (volume ratio)) to obtain 8.29 g of (7Z,10Z,13Z)-hexadecatrien-16-olide having a GC purity of 96.8% (yield 64.0% th). The structure thereof was confirmed by NMR.

¹H NMR (500 MHz, CDCl₃) δppm:
5.55-5.35 (6H, m), 4.16 (2H, t, J=5.9 Hz), 2.85 (2H, t, J=6.7 Hz), 2.81 (2H, t, J=6.3 Hz), 2.38-2.41 (2H, m), 2.29 (2H, t, J=7.1 Hz), 2.04-2.08 (2H, m), 1.62-1.67 (2H, m), 1.32-1.37 (4H, m).

Example 2

Synthesis of (6Z,9Z,12Z)-tetradecatrien-14-olide [Formula (1); m=4, n=1]

(6Z,9Z,12Z)-Tetradecatrien-14-olide was synthesized in the same manner as in Example 1 except that methyl 6-heptynoate was used as a compound of (II) and 2-propyn-1-ol was used as a compound of (V). The used amounts (mol, equivalent, and time(s) content) were same as the case of Example 1. The results of purity and NMR of products of respective processes are given as follows.

Methyl 14-hydroxytetradeca-6,9,12-triynoate [Formula (2); m=4, n=1, R=methyl]

GC purity 96.7%
¹H NMR (500 MHz, CDCl₃) δppm:
4.26 (2H, s), 2.08 (3H, s), 3.20-3.21 (2H, m), 3.12-3.14 (2H, m), 2.10-2.35 (1H, bs), 2.34 (2H, t, J=7.6 Hz), 2.17-2.21 (2H, m), 1.70-1.74 (2H, m), 1.51-1.54 (2H, m).

Methyl 14-Hydroxytetradeca-(6Z,9Z,12Z)-trienoate [Formula (3); m=4, n=1, R=methyl]

GC purity: 96.2%
¹H NMR (500 MHz, CDCl₃) δppm:
5.33-5.66 (6H, m), 4.19 (2H, m), 3.68 (3H, s), 2.77-2.88 (4H, m), 2.31 (2H, t, J=7.5 Hz), 2.06-2.10 (2H, m), 2.02-2.05 (1H, bs), 1.36-1.43 (4H, m).

(6Z,9Z,12Z)-Tetradecatrien-14-olide [Formula (1); m=4, n=1]

GC purity: 97.7%
¹H NMR (500 MHz, CDCl₃) δppm:
5.34-5.69 (6H, m), 4.61-4.63 (2H, m), 2.93-2.95 (2H, m), 2.80-2.82 (2H, m), 2.38-2.41 (2H, m), 1.99-2.04 (2H, m), 1.72-1.77 (2H, m), 1.36-1.42 (2H, m).

Example 3

Synthesis of (6Z,9Z,12Z)-pentadecatrien-15-olide [Formula (1); m=4, n=2]

(6Z,9Z,12Z)-Pentadecatrien-15-olide was synthesized in the same manner as in Example 1 except that methyl 6-heptynoate was used as a compound of (II). The used amounts (mol, equivalent, and time(s) content) were same as the case of Example 1. The results of purity and NMR of products of respective processes are given as follows.

Methyl 15-hydroxypentadeca-6,9,12-triynoate [Formula (2); m=4, n=2, R=methyl]

GC purity: 97.8%
¹H NMR (500 MHz, CDCl₃) δppm:
3.71 (2H, t, J=6.2 Hz), 3.68 (3H, s), 3.12-3.19 (4H, m), 2.43-2.46 (2H, m), 2.33 (2H, t, J=7.5 Hz), 2.17-2.21 (2H, m), 1.90-2.15 (1H, bs), 1.69-1.75 (2H, m), 1.51-1.36 (2H, m).

Methyl 15-Hydroxypentadeca-(6Z,9Z,12Z)-trienoate
[Formula (3); m=4, n=2, R=methyl]

GC purity: 98.1%
$^1$H NMR (500 MHz, CDCl$_3$) δppm:
5.35-5.67 (6H, m), 3.67 (3H, s), 3.64-3.68 (2H, m), 2.80-2.87 (4H, m), 2.30-2.39 (4H, m), 2.04-2.11 (2H, m), 2.04-2.11 (1H, bs), 1.36-1.43 (4H, m).

(6Z,9Z,12Z)-Pentadecatrien-15-olide [Formula (1); m=4, n=2]

GC purity: 98.0%
$^1$H NMR (500 MHz, CDCl$_3$) δppm:
5.33-5.55 (6H, m), 4.16-4.19 (2H, m), 2.80-2.85 (2H, m), 2.37-2.42 (2H, m), 2.27-2.34 (2H, m), 2.04-2.10 (2H, m), 1.65-1.70 (2H, m), 1.32-1.44 (4H, m).

Example 4

Synthesis of (7Z,10Z,13Z)-pentadecatrien-15-olide
[Formula (1); m=5, n=1]

(7Z,10Z,13Z)-Pentadecatrien-15-olide was synthesized in the same manner as in Example 1 except that 2-propyn-1-ol was used as a compound of (V). The used amounts (mol, equivalent, and time(s) content) were same as the case of Example 1. The results of purity and NMR of products of respective processes are given as follows.

Methyl 15-hydroxypentadeca-7,10,13-triynoate
[Formula (2); m=5, n=1, R=methyl]

GC purity: 96.5%
$^1$H NMR (500 MHz, CDCl$_3$) δppm:
4.26 (2H, s), 3.67 (3H, s), 3.12-3.21 (4H, m), 2.33 (2H, t, J=7.6 Hz), 2.31-2.34 (1H, bs), 2.15-2.19 (2H, m), 1.39-1.67 (6H, m).

Methyl 15-hydroxypentadeca-(7Z,10Z,13Z)-trienoate
[Formula (3); m=5, n=1, R=methyl]

GC purity: 95.3%
$^1$H NMR (500 MHz, CDCl$_3$) δppm:
5.33-5.55 (6H, m), 4.23-4.24 (2H, m), 2.07 (3H, s), 2.79-2.88 (4H, m), 2.31 (2H, t, J=7.5 Hz), 2.04-2.09 (2H, m), 1.48-1.61 (1H, bs), 1.32-1.67 (6H, m).

(7Z,10Z,13Z)-Pentadecatrien-15-olide [Formula (1); m=5, n=1]

GC purity: 96.2%
$^1$H NMR (500 MHz, CDCl$_3$) δppm:
5.31-5.73 (6H, m), 4.54-4.59 (2H, m), 2.79-2.94 (2H, m), 2.30-2.38 (2H, m), 1.99-2.07 (2H, m), 1.61-1.70 (2H, m), 1.29-1.47 (6H, m).

Example 5

Synthesis of (5Z,8Z,11Z)-hexadecatrien-16-olide
[formula (1); m=3, n=4]

(5Z,8Z,11Z)-Hexadecatrien-16-olide was synthesized in the same manner as in Example 1 except that methyl 5-hexynoate was used as a compound of (II) and 5-hexyn-1-ol was used as a compound of (V). The used amounts (mol, equivalent, and time(s) content) were same as the case of Example 1. The results of purity and NMR of products of respective processes are given as follows.

Methyl 16-Hydroxyhexadeca-5,8,11-triynoate
[Formula (2); m=3, n=4, R=methyl]

GC purity: 91.9%
$^1$H NMR (500 MHz, CDCl$_3$) δppm:
3.66-3.70 (2H, m), 3.68 (3H, s), 3.12-3.14 (4H, m), 2.44 (2H, t, J=7.5 Hz), 2.19-2.25 (4H, m), 1.78-1.85 (2H, m), 1.78-1.85 (1H, bs), 1.55-1.70 (4H, m).

Methyl 16-Hydroxyhexadeca-(5Z,8Z,11Z)-trienoate
[formula (3); m=3, n=4, R=methyl]

GC purity: 91.1%
$^1$H NMR (500 MHz, CDCl$_3$) δppm:
5.34-5.43 (6H, m), 3.67 (3H, s), 3.65 (2H, t, J=6.6 Hz), 2.79-2.82 (4H, m), 2.33 (2H, t, J=7.5 Hz), 2.06-2.14 (4H, m), 2.06-2.14 (1H, bs), 1.67-1.74 (2H, m), 1.41-1.57 (4H, m).

(5Z,8Z,11Z)-Hexadecatrien-16-olide [Formula (1); m=3, n=4]

GC purity: 96.9%
$^1$H NMR (500 MHz, CDCl$_3$) δppm:
4.12-4.17 (6H, m), 4.16 (2H, t, J=6.1 Hz), 2.79-2.82 (4H, m), 2.33-2.36 (2H, m), 2.07-2.11 (4H, m), 1.68-1.73 (4H, m), 1.43-1.49 (4H, m).

Example 6

Synthesis of (6Z,9Z,12Z)-Hexadecatrien-16-olide
[Formula (1); m=4, n=3]

(6Z,9Z,12Z)-Hexadecatrien-16-olide was synthesized in the same manner as in Example 1 except that methyl 6-heptynoate was used as a compound of (II) and 4-Pentyn-1-ol was used as a compound of (V). The used amounts (mol, equivalent, and time(s) content) were same as the case of Example 1. The results of purity and NMR of products of respective processes are given as follows.

Methyl 16-Hydroxyhexadeca-6,9,12-triynoate
[Formula (2); m=4, n=3, R=methyl]

GC purity: 95.4%
$^1$H NMR (500 MHz, CDCl$_3$) δppm:
3.75 (2H, t, J=6.2 Hz), 3.67 (3H, s), 3.13-3.14 (4H, m), 2.33 (2H, t, J=7.4 Hz), 2.28-2.31 (2H, m), 2.17-2.21 (2H, m), 1.65-1.90 (1H, bs), 1.69-1.78 (4H, m), 1.51-1.56 (2H, m).

Methyl 16-Hydroxyhexadeca-(6Z,9Z,12Z)-trienoate
[Formula (3); m=4, n=3, R=methyl]

GC purity: 95.4%
$^1$H NMR (500 MHz, CDCl$_3$) δppm:
5.35-5.65 (6H, m), 3.67 (3H, s), 3.64-3.66 (2H, m), 2.80-2.83 (4H, m), 2.31-2.34 (2H, m), 2.07-2.19 (4H, m), 2.07-2.19 (1H, bs), 1.62-1.68 (4H, m), 1.35-1.42 (2H, m).

(6Z,9Z,12Z)-Hexadecatrien-16-olide [Formula (1); m=4, n=3]

GC purity: 96.1%
$^1$H NMR (500 MHz, CDCl$_3$) δppm:

5.32-5.47 (6H, m), 4.09-4.11 (2H, m), 2.81-2.84 (4H, m), 2.36 (2H, t, J=7.2 Hz), 2.04-2.21 (4H, m), 1.34-1.74 (6H, m).

Example 7

Sensory Evaluation

With respect to Z-form compounds represented by the formula (1) produced in Examples 1 to 6, sensory evaluation of odor was performed by professional panelists. The results are shown in Table 1.

TABLE 1

| | Compound represented by the formula (1) | m | n | Aroma note |
|---|---|---|---|---|
| Example 1 | (7Z,10Z,13Z)-Hexadecatrien-16-olide | 5 | 2 | Fruity and natural musky note |
| Example 2 | (6Z,9Z,12Z)-Tetratadecatrien-14-olide | 4 | 1 | Musky note with freshness and floral-like character |
| Example 3 | (6Z,9Z,12Z)-Pentadecatrien-15-olide | 4 | 2 | Unique musky note with elegant creaminess (mositureness). Slightly animalic. |
| Example 4 | (7Z,10Z,13Z)-Pentadecatrien-15-olide | 5 | 1 | Clear and impactive floral-musky note. |
| Example 5 | (5Z,8Z,11Z)-Hexadecatrien-16-olide | 3 | 4 | Musky note with soft creaminess and fruitiness evocative of γ-undecalactone |
| Example 6 | (6Z,9Z,12Z)-Hexadecatrien-16-olide | 4 | 3 | Musky note with rich powdery, creamy and animalic nuance |

The compound represented by the formula (1) of the present invention had a unique musk aroma.

Example 8

Preparation of Fragrance Composition

A fruity/floral-type fragrance composition was prepared in accordance with the prescription shown in Table 2.

TABLE 2

| | wt % |
|---|---|
| Apple-peach base | 40 |
| Dipropylene glycol | 0.4 |
| Ethyl methyl phenyl glycidate | 2 |
| Hedione | 10 |
| β-Ionone | 3 |
| L-Citronellol | 3 |
| Linalool | 18 |
| 8 wt % DPG* solution of mercaptomenthone | 0.2 |
| Orange terpene | 8 |
| γ-Undecalactone | 5 |
| Ethyl maltol | 0.4 |
| 10 wt % DPG of solution (7Z,10Z,13Z)-hexadecatrien-16-olide obtainedin Example 1 | 10 |
| Sum | 100 |

*In Table 2, DPG represents dipropylene glycol.

Example 9

Preparation of Shampoo

A shampoo to which the fruity/floral-type fragrance composition obtained in Example 8 was added at a ratio of 0.3% was prepared by a common method. The prescription details are shown in Table 3. The obtained shampoo suitably had a musk aroma.

TABLE 3

| | wt % |
|---|---|
| Sodium lauryl polyoxyethylene ether sulfate | 14 |
| Amide propyl betaine laurate | 4 |
| Coconut fatty acid diethanolamide | 3 |
| Cationized cellulose | 0.5 |
| Ethylene glycol distearate | 1 |
| Paraoxybenzoic acid ester | 0.25 |
| Citric acid | suitable amount |
| Fragrance composition of Example 8 | 0.3 |
| Purfied water | balance |
| Sum | 100 |

Example 10

Preparation of Conditioner

A conditioner to which the fruity/floral-type fragrance composition obtained in Example 8 was added at a ratio of 0.3% was prepared by a common method. The details of prescription are shown in Table 4. The obtained conditioner suitably had a musk aroma.

TABLE 4

| | wt % |
|---|---|
| Stearyl trimethyl ammonium chloride | 0.5 |
| Ammonium distearyl dimethyl chloride | 1.5 |
| Jojoba oil | 2.5 |
| Cetanol | 4.5 |
| Liquid lanolin | 2 |
| Polyoxyethylene stearyl ether | 1.5 |
| Concentrated glycerin | 7 |
| Paraoxybenzoic acid ester | 0.25 |
| Sodium hydroxide | suitable amount |
| Citric acid | suitable amount |
| Fragrance composition of Example 8 | 0.3 |
| Purified water | balance |
| Sum | 100 |

Example 11

Preparation of Flavor or Fragrance Composition

A flavor composition was prepared in accordance with the prescription of Table 5 below.

TABLE 5

| | Parts by weight |
|---|---|
| Ethyl acetate | 11 |
| cis-3-Hexenol | 3 |
| Hexanol | 5 |
| Benzaldehyde | 2 |
| Ethyl hexanoate | 22 |
| cis-3-Hexenyl acetate | 2 |
| Linalool | 70 |
| Linalool oxide | 4 |
| Hexyl butyrate | 25 |
| Hexyl hexanoate | 15 |
| α-Terpineol | 5 |
| Citral | 15 |

TABLE 5-continued

| | Parts by weight |
|---|---|
| cis-3-Hexenyl butyrate | 4 |
| cis-3-Hexenyl hexanoate | 5 |
| β-Ionone | 6 |
| Ethyl butyrate | 10 |
| 8-Mercapto menthone | 0.01 |
| (6Z,9Z,12Z)-Tetradecatrien-14-olide obtained in Example 2 | 0.01 |
| 95% ethanol | balance |
| Sum | 1000 |

Example 12

Preparation of Carbonated Drink

A carbonated drink (Brix 9.3, acidity: 0.13% (based on citric acid), pH 3.4, gas volume: 3.0) was prepared using the flavor or fragrance composition prepared in Example 11 in accordance with the prescription shown in the following Table 6. In addition, a carbonated drink was prepared as a control using the flavor composition prepared in the same manner as in Example 11, except that (6Z,9Z,12Z)-tetradecatrien-14-olide obtained in Example 2 was not added.

The obtained carbonated drink had a remarkably highly fresh and natural fruity note as compared to the control carbonated drink.

TABLE 6

| | Parts by weight |
|---|---|
| Fructose glucose liquid sugar | 93.9 |
| Granulated sugar | 20.0 |
| Anhydrous citric acid | 1.3 |
| Flavor or fragrance composition prepared in Example 11 | 1.0 |
| Sodium citrate | 0.1 |
| Water | 200 |
| Carbonated water | 783.7 |
| Sum | 1100 |

While the invention has been described in detail and with reference to specific embodiments thereof, it will be apparent to one skilled in the art that various changes and modifications can be made therein without departing from the spirit and scope thereof.

This application is based on Japanese Patent Application No. 2011-040574 filed on Feb. 25, 2011, the entire subject matter of which is incorporated herein by reference. In addition, all documents cited in the specification are also incorporated herein by reference.

INDUSTRIAL APPLICABILITY

The compound of the present invention represented by the formula (1) has a unique musk aroma such as fruit-like, floral-like, creamy-like and animal-like aroma. The compound can impart the desired fragrances and flavors to various products such as food products or beverages, fragrances or cosmetics, daily necessities and household goods and oral products, and is thus useful.

In addition, by adding a small amount of the compound of the present invention represented by the formula (1) to various products, fragrances and flavors such as naturalness, freshness and fruitiness can be imparted to the products.

The production method of the present invention is useful in that a Z-form of the compound represented by the formula (1) can be selectively produced at a high purity.

The invention claimed is:

1. A compound represented by the following formula (1):

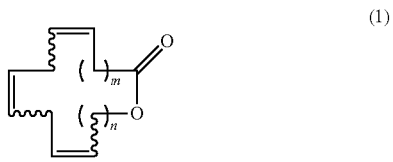

(1)

wherein each of wavy lines represents an Z-configuration of C=C double bond; m represents an integer of 0 to 10; and n represents an integer of 1 to 11, wherein n represents an integer of 1 to 11 when m is 0 to 4 or 6 to 10; and n is an integer of 1 or 3 to 11 when m is 5.

2. A method for producing a compound represented by the following formula (1),

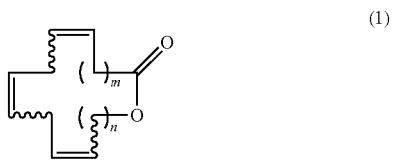

(1)

wherein each of wavy lines represents an Z-configuration of C=C double bond; m represents an integer of 0 to 10; and n represents an integer of 1 to 11, which comprises:
hydrogenating an ω-hydroxytriyne esters represented by the following formula (2):

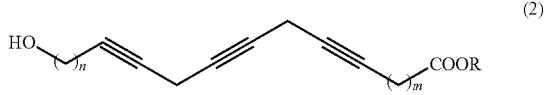

(2)

wherein m represents an integer of 0 to 10; n represents an integer of 1 to 11; and R represents a monovalent aromatic ring group having 6 to 20 carbon atoms, or a monovalent hydrocarbon group having 1 to 20 carbon atoms which may have a substituent group;

and lactonizing an ω-hydroxytriene esters represented by the following formula (3) obtained by the hydrogenation:

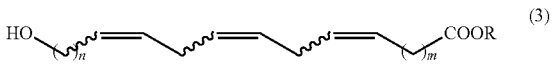

(3)

wherein m represents an integer of 0 to 10; n represents an integer of 1 to 11; and R represents a monovalent aromatic ring group having 6 to 20 carbon atoms, or a monovalent hydrocarbon group having 1 to 20 carbon atoms which may have a substituent group, and each of wavy lines represents at least one of an E-configuration of C=C double bond and an Z-configuration of C=C double bond.

3. The method according to claim 2, wherein the compound represented by the formula (1) is produced in a ratio of 95% or more based on the whole of the produced compounds represented by the formula (1), and the rest can either be geometrical isomers.

4. The method according to claim 2, wherein the ω-hydroxytriene esters represented by the formula (3) is lactonized with titanate.

5. A flavor or fragrance composition comprising the compound according to claim 1.

6. A product comprising the compound according to claim 1, wherein the product is selected from the group consisting of a food product or beverage, a fragrance or cosmetic, a daily necessities and household goods and an oral product.

7. A product comprising the flavor or fragrance composition according to claim 5, wherein the product is selected from the group consisting of a food product or beverage, a fragrance or cosmetic, a daily necessities and household goods and an oral product.

8. The compound according to claim 1, which has a musk aroma.

9. The method according to claim 3, wherein the ω-hydroxytriene esters represented by the formula (3) is lactonized with titanate.

10. A flavor or fragrance composition comprising the compound according to claim 8.

11. A product comprising the compound according to claim 8, wherein the product is selected from the group consisting of a food product or beverage, a fragrance or cosmetic, a daily necessities and household goods and an oral product.

12. A product comprising the flavor or fragrance composition according to claim 10, wherein the product is selected from the group consisting of a food product or beverage, a fragrance or cosmetic, a daily necessities and household goods and an oral product.

* * * * *